United States Patent [19]

Theissen

[11] 4,340,417
[45] Jul. 20, 1982

[54] HERBICIDAL 1-(5-[2-CHLORO-4-(TRIFLUOROMETHYL)-PHENOXY]-2-NITROBENZOYL)-3-ISOPROPYL-2,1,3-BENZOTHIADIAZIN-4-ONE,2,2-DIOXIDE

[75] Inventor: Robert J. Theissen, Bridgewater, N.J.

[73] Assignee: Rhone-Poulenc Agrochimie, Lyons, France

[21] Appl. No.: 276,619

[22] Filed: Jun. 23, 1981

Related U.S. Application Data

[63] Continuation-in-part of Ser. No. 117,732, Feb. 1, 1980, abandoned.

[51] Int. Cl.³ .................. C07D 285/16; A01N 43/88
[52] U.S. Cl. .................................... 71/91; 544/11
[58] Field of Search .......................... 544/11; 71/91

[56] References Cited

U.S. PATENT DOCUMENTS

| | | | |
|---|---|---|---|
| 3,041,336 | 6/1962 | Teufel | 544/11 |
| 4,139,700 | 2/1979 | Kloek | 544/11 |
| 4,208,514 | 6/1980 | McKendry | 544/11 |
| 4,209,318 | 6/1980 | Johnson . | |
| 4,285,723 | 8/1981 | Cartwright et al. . | |

FOREIGN PATENT DOCUMENTS 20052 12/1980 European Pat. Off. .
54-151943 11/1979 Japan .

*Primary Examiner*—John M. Ford
*Attorney, Agent, or Firm*—Morgan, Finnegan, Pine, Foley & Lee

[57] ABSTRACT

There is provided herbicidal 1-(5-[2-chloro-4-(trifluoromethyl)phenoxy]-2-nitrobenzoyl)-3-isopropyl-2,1,3-benzothiadiazin-4-one-2,2-dioxide. This compound is particularly useful when applied in a post-emergence application to soybean fields containing broadleaf weeds.

4 Claims, No Drawings

HERBICIDAL 1-(5-[2-CHLORO-4-(TRIFLUOROMETHYL)-PHENOXY]-2-NITROBENZOYL)-3-ISOPROPYL-2,1,3-BENZOTHIADIAZIN-4-ONE,2,2-DIOXIDE

CROSS REFERENCE TO RELATED APPLICATIONS

This application is a continuation-in-part of U.S. Application Ser. No. 117,732, filed Feb. 1, 1980, now abandoned.

BACKGROUND OF THE INVENTION

The invention is concerned with herbicidal 1-(5-[2-chloro-4-(trifluoromethyl)phenoxy]-2-nitrobenzoyl)-3-isopropyl-2,1,3-benzothiadiazin-4-one-2,2-dioxide.

The compound 3-isopropyl-2,1,3-benzothiadiazin-4-one-2,2-dioxide, including the salt forms thereof is known to have herbicidal activity (note U.S. Pat. No. 4,116,672). The compound, 5-[2-chloro-4-(trifluoromethyl)phenoxy]-2-nitrobenzoic acid, including the salt forms thereof, is known to have herbicidal activity. According to a particular herbicidal treatment, it has been proposed to apply this compound in a post-emergence fashion to control weeds, especially broadleaf weeds, in soybean fields. Accordingly, in such an application, a herbicide must possess the following two properties at the applied dosage rate: (1) the ability to control the target weeds; and (2) the ability to remain safe to the soybeans.

In attempting to improve on the herbicidal properties of 5-[2-chloro-4-(trifluoromethyl)phenoxy]-2-nitrobenzoic acid and salts thereof, various derivatives of these compounds have been proposed including alkyl and cycloalkyl esters, alkylthio esters, phenyl ester, alkyl and dialkyl amido and benzoyl chloride forms. U.S. Pats. which describe such compounds and the like include Nos. 3,652,645; 3,784,635; 3,873,302; 3,983,168; 3,907,866; 3,798,276; 3,928,416; and 4,063,929. For example, the simple methyl ester of the above-mentioned acid, i.e., methyl 5-[2-chloro-4-(trifluoromethyl)-phenoxy]-2-nitrobenzoate, has been proposed, and it has been discovered that this compound has even greater herbicidal activity than 5-[2-chloro-4-(trifluoromethyl)-phenoxy]-2-nitrobenzoic acid with respect to various weeds, e.g. broadleaf weeds. However, it has also been discovered that methyl 5-[2-chloro-4-(trifluoromethyl)-phenoxy]-2-nitrobenzoate has a relatively large degree of post-emergence herbicidal activity with respect to crops. Consequently, methyl 5-[2-chloro-4-(trifluoromethyl)phenoxy]-2-nitrobenzoate should not be applied in a post-emergence fashion to control broadleaf weeds in soybeans, because this compound tends to kill soybeans along with the weeds in such applications.

Accordingly, there is a need in the art for compounds which have a desirable combination of herbicidal properties with respect to weed activity and crop safety.

SUMMARY OF THE INVENTION

This invention provides certain herbicidal compounds of the formula:

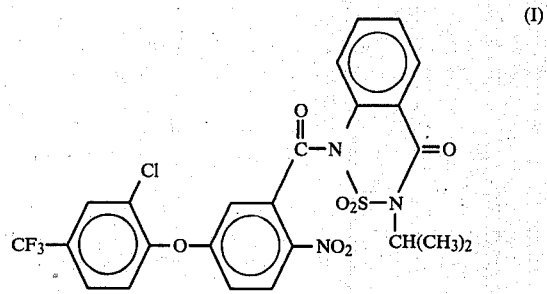

(I)

EXAMPLE

Preparation of 1-[5-(2-chloro-4-(trifluoromethyl)-phenoxy)-2-nitrobenzoyl]-3-isopropyl-2,1,3-benzothiadiazin-4-one-2,2-dioxide.

To a stirred solution of 3-isopropyl-2,1,3-benzothiadiazin-4-one-2,2-dioxide (2.4 g, 0.01 mole) and triethylamine (1.1 g, 0.011 mole) in a mixture of toluene (100 ml) and chloroform (100 ml) was added 5-[2-chloro-4-(trifluoromethyl)phenoxy]-2-nitrobenzoyl chloride (3.8 g, 0.01 mole). The reaction was heated for 24 hours and then the solvent was removed. The residue was taken back up into chloroform and extracted three times with sodium hydroxide and finally with water. The organic solution was dried and evaporated to give 2.8 g of an oil which was triturated with petroleum ether to give a solid which was recrystallized from chloroform-petroleum ether to give a white solid, mp 125°–8° C.

IR(nujol): C=O, 1740 and 1710 cm$^{-1}$

The compound of this invention can be applied in various ways to achieve herbicidal action. It can be applied per se, as solids or in vaporized form, but is preferably applied as the toxic components in pesticidal compositions of the compound and a carrier. This composition may be applied directly to the soil and often incorporated therewith. The compositions can be applied as granulars or dusts; as liquid sprays, or as gas-propelled sprays and can contain, in addition to a carrier, additives such as emulsifying agents, binding agents, gases compressed to the liquid state, odorants, stabilizers, and the like. A wide variety of liquid and solid carriers can be used. Non-limiting examples of solid carriers include talc, bentonite, diatomaceous earth, pyrophyllite, fullers earth, gypsum, flours derived from cotton seeds and nut shells, and various natural and synthetic clays having a pH not exceeding about 9.5. Non-limiting examples of liquid carriers include water, organic solvents such as alcohols, ketones, light oils, and medium oils and vegetable oils such as cottonseed oil.

In practice, herbicidal application is measured in terms of pounds of herbicide applied per acre. The compound of this invention is effective herbicides when applied in herbicidal amounts, i.e., at rates between about 0.03 pound and about 10 pounds per acre.

Herbicidal Effectiveness

Method of Propagating Test Species

Crop and weed species are planted in 8"×10" disposable fiber flats containing potting soil to provide each flat with a 4" row of all test species. Crop species consist of field corn (CN), cotton (CT), and soybeans (SB). The weed species consist of foxtail millet (FM), green foxtail (GF), velvetleaf (VL), cocklebur (CB), wild mustard (WM) and pigweed (PW).

Cotton, corn, soybean, and cocklebur plantings consist of 4 to 5 seeds per row depending upon species. The smaller seeded species (velvetleaf, wild mustard, pigweed, foxtail millet and green foxtail) are planted in an uncounted but sufficient number to provide a solid row of seedlings.

Plantings for the pre- and post-emergence portions of the test are identical as to seeding. The initial watering until emergence is done from the top. The post-emergence phase is propagated in advance so as to provide plants of the proper stage of development at the time of treatment. Plantings for the pre-emergence phase are made not more than one day in advance of treatment.

The desired stage of development for treatment of the post-emergence broadleaf species (CT, SB, CB, VL, WM, PW) is the one true leaf or first trifoliate leaf stage. The desired stage for corn would be a height of 3-4", while a 2" height would be adequate for the grasses.

Method of Treatment

Spray applications are made with a handgun sprayer (aspirator type) simultaneously to one flat of established plants for the post-emergence phase and one newly seeded flat for the pre-emergence phase. A 10 lb./acre treatment rate consists of the uniform application of 116 milligrams of test compound to the combined area of the two flats (160 sq. inches). Application is made in a solvent mixture consisting of 40 ml acetone and 40 ml water and a surfactant concentration of 0.1 percent.

Following spray application, flats are returned to the greenhouse where watering of the post-emergence phase is done only by subirrigation. The pre-emergence phase is top watered by sprinkling until after test species have emerged. Subsequent watering is by subirrigation.

Two weeks after treatment, the pre- and post-emergence injury and control is rated on a 0-100 percent injury and control scale. Special physiological effects are rated as to intensity also at this time.

The herbicidal test data is reported for the compound of this invention and was obtained at application rates of 2 lbs. and ½ lb/acre. The following lists the metric equivalents for rates expressed in terms of lbs/acre.

| Application Rate | |
|---|---|
| US - lb./acre | Metric - kg/ha |
| 10.0 | 11.2 |
| 4.0 | 4.48 |
| 2.0 | 2.24 |
| 1.0 | 1.12 |
| 0.5 | 0.56 |
| 0.25 | 0.28 |
| 0.125 | 0.14 |
| 0.0625 | 0.07 |

Test results are set forth in Table I pre-emergence and post-emergence.

| Dosage Lbs./Acre | Pre-Emergence | | | | | | | | | Post-Emergence | | | | | | | | |
|---|---|---|---|---|---|---|---|---|---|---|---|---|---|---|---|---|---|---|
| | FM | GF | VL | CB | WM | PW | CT | CN | SB | FM | GF | VL | CB | WM | PW | CT | CN | SB |
| 2 | 100 | 90 | 10 | 0 | 100 | 90 | 0 | 0 | 0 | 90 | 90 | 100 | 90 | 100 | 100 | 50 | 20 | 30 |
| ½ | 90 | 70 | 0 | 10 | 90 | 60 | 10 | 0 | 0 | 90 | 90 | 90 | 80 | 100 | 100 | 30 | 10 | 30 |

The compound of the present invention may be particularly advantageous when used to control weeds in field of crops which are relatively tolerant thereto. For instance, the foregoing data demonstrates that certain crop species are more tolerant to these compounds than certain grass or broadleaf weed species. The herbicidal compound of the present invention is particularly useful when applied in post-emergence applications to control broadleaf weeds, e.g., velvetleaf, cocklebur, wild mustard and pigweed, in soybean fields.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A herbicidal compound of the formula

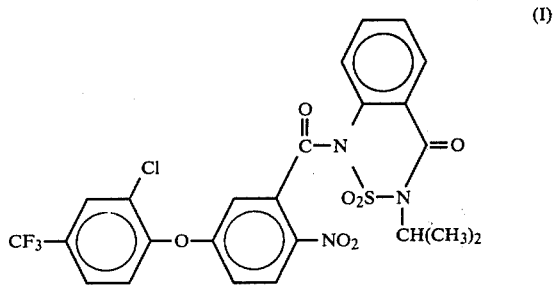

2. A method for combating unwanted plants which comprises contacting them with a herbicidally effective amount of a compound according to claim 1.

3. A method according to claim 2 wherein said compound is applied in a post-emergence application to a field comprising soybean plants and at least one broadleaf weed species.

4. A method according to claim 3 wherein said boradleaf weed species comprise at least one species selected from the group consisting of velvetleaf, cocklebur, wild mustard and pigweed.

* * * * *

UNITED STATES PATENT AND TRADEMARK OFFICE
CERTIFICATE OF CORRECTION

PATENT NO. : 4,340,417
DATED : Jul. 20, 1982
INVENTOR(S) : Robert J. Theissen

It is certified that error appears in the above-identified patent and that said Letters Patent is hereby corrected as shown below:

At column 4, line 59 "borad" should read -- broad- --.

Signed and Sealed this

Twelfth Day of April 1983

[SEAL]

Attest:

GERALD J. MOSSINGHOFF

Attesting Officer     Commissioner of Patents and Trademarks